United States Patent [19]

Kondo et al.

[11] 4,268,442

[45] May 19, 1981

[54] PROCESS FOR PREPARING AROMATIC ACETIC ACID

[75] Inventors: Kiyosi Kondo; Tamotsu Fujimoto, both of Yamato; Minoru Suda; Daiei Tunemoto, both of Sagamihara, all of Japan

[73] Assignee: Sagami Chemical Research Center, Tokyo, Japan

[21] Appl. No.: 93,818

[22] Filed: Nov. 13, 1979

[30] Foreign Application Priority Data

Nov. 14, 1978 [JP] Japan .................. 53-139364
Nov. 14, 1978 [JP] Japan .................. 53-139365

[51] Int. Cl.$^3$ ............. C07C 53/132; C07D 207/337; C07D 307/54; C07D 333/24
[52] U.S. Cl. ...................... 260/326.2; 562/465; 562/466; 562/490; 562/496; 549/72; 549/79; 260/326.47; 260/347.3; 260/340.5 R
[58] Field of Search ............ 562/496, 490, 465, 466; 560/105; 549/79, 72; 260/326.2, 326.47, 347.3, 340.5 R

[56] References Cited

FOREIGN PATENT DOCUMENTS 2810262 9/1978 Fed. Rep. of Germany.

OTHER PUBLICATIONS

Reeve, Wilkins et al. *J. Am. Chem. Soc.*, vol. 83, pp. 2755–2759 (1961).

*Primary Examiner*—Natalie Trousof
*Assistant Examiner*—L. Hendriksen
*Attorney, Agent, or Firm*—Frishauf, Holtz, Goodman & Woodward

[57] ABSTRACT

There are disclosed processes for preparing an aromatic acetic acid by the reaction of an aromatic aldehyde with a combination of a trihalomethane and an alkanethiol, and by the reaction of an alcohol derivative (2,2,2-trihalo-1-arylethanol) with an alkanethiol, in the presence of a base in a mixed medium of water and an aprotic polar solvent.

22 Claims, No Drawings

PROCESS FOR PREPARING AROMATIC ACETIC ACID

This invention relates to novel processes for preparing an aromatic acetic acid. More particularly, this invention relates to novel processes for preparing an aromatic acetic acid starting from an aromatic aldehyde and a combination of a trihalomethane and an alkanethiol, or an alcohol derivative (2,2,2-trihalo-1-arylethanol and an alkanethiol, in the presence of a base in a mixed medium of water and an aprotic polar solvent.

Certain types of substituted aromatic acetic acids have been known to exhibit antipyretic, anti-inflammatory, analgesic and antispasmodic activities and have been practically used as pharmaceuticals. Also, some of the aromatic acetic acids are utilized as chemical modifier for antibiotics and, in addition, are used as raw materials for the production of a new type of synthetic pyrethroids. Accordingly, development of a novel process for preparing these useful substituted aromatic acetic acids by a simple procedure will greatly contribute to the chemical industry.

Hitherto, the above type of compounds have been prepared by the following processes:

(1) Process comprising heating a halobenzene and an α-haloacetate in the presence of copper powder [refer to Th. Zincke, Ber., 2, 738 (1869)].

(2) Process comprising converting a benzyl halide as a raw material into a Grignard reagent followed by carboxylation [refer to J. Houben, Ber., 35, 2523 (1902)].

(3) Process by Arndt-Eistert-Wolff reaction of diazoacetophenone [refer to L. Wolff, Ann., 394, 43 (1912)].

(4) Process comprising acetylating an aromatic compound followed by heating together with ammonium polysulfide and then hydrolysis [W. E. Bachmann et al., J. Amer. Chem. Soc., 65, 1329 (1943)].

(5) Process comprising treating a benzyl halide with sodium cyanide, potassium cyanide or the like to form an aromatic substituted acetonitril which is then hydrolyzed with an alkali or an acid into an aromatic acetic acid [refer to A. W. Hofmann, Ber., 7, 519 (1874); R. Adams and A. F. Thal, Org. Synth., Coll. Vol. I, 436 (1947)].

(6) Process comprising reacting an aromatic aldehyde with formaldehyde mercaptal S-oxide followed by treating with a mineral acid to convert into an aromatic acetic acid derivative [refer to K. Ogura et al., Tetra. Letters, 1383 (1972)].

(7) Process comprising synthesis of an aromatic acid by treating a 2,2,2-trihalo-1-arylethanol with water, an alcohol, a mercaptan or an amine in the presence of a base to prepare the corresponding an α-oxy, α-thio or α-amino-substituted aromatic acetic acid and removing the α-substituent by reduction procedure [refer to Japanese Provisional Patent Publication (Japan KOKAI) Nos. 112836/1978 and 112868/1978].

However, in the processes (1) and (4), the reaction conditions are very difficult to determine and also the reaction yield is generally low. In carrying out the process (2), anhydrous reaction condition must be established. The process (3) requires unstable diazo compounds as starting materials. In the process (5), the starting material benzyl halides are not easily available and, in addition, the process must be performed by the use of a highly toxic cyanide as a starting material. The process (6) requires a number of reaction steps. The process (7) also requires a number of reaction steps since the process requires the synthesis of an α-substituted-phenylacetic acid and then reduction.

Such disadvantages associated with these conventional processes prevent the practical use of these conventional processes in industry and, in general, when substituents to be retained on the aromatic ring have to be introduced beforehand into the aromatic ring, these conventional processes cannot easily be used practically.

An object of this invention is to provide a novel process for preparing in high yield and selectivity an aromatic acetic acid starting from an aromatic aldehyde.

Another object of this invention is to provide a novel process for preparing in high yield and selectivity an aromatic acetic acid starting from an alcohol derivative (2,2,2-trihalo-1-arylethanol), which alcohol may also be isolated as an intermediate compound in the reaction in which the aromatic aldehyde is used as a starting material.

A process according to this invention is a process for preparing an aromatic acetic acid represented by formula (I)

$$ArCH_2COOH \qquad (I)$$

wherein Ar is a substituted or unsubstituted aromatic group,
which comprises reacting an aromatic aldehyde represented by formula (II)

$$ArCHO \qquad (II)$$

wherein Ar has the same meaning as defined above,
with a trihalomethane represented by formula (IV)

$$HCX_3 \qquad (IV)$$

wherein X represents a halogen atom,
in the presence of a base in a mixed medium of water and an aprotic polar solvent to form an alcohol derivative represented by formula (III)

$$Ar-\underset{\underset{OH}{|}}{CH}-CX_3 \qquad (III)$$

wherein Ar has the same meaning as defined above,
and then reacting the thus formed alcohol derivative with an alkanethiol represented by formula (V)

$$RSH \qquad (V)$$

wherein R is an alkyl group,
in the presence of a base in a mixed medium of water and an aprotic polar solvent.

Another process of this invention is a process for preparing an aromatic acetic acid represented by formual (I)

$$ArCH_2COOH \qquad (I)$$

wherein Ar has the same meaning as defined above
which comprises reacting an alcohol derivative represented by formula (III)

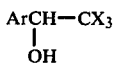 (III)

wherein Ar and X have the same meanings as defined above,
with an alkanethiol represented by formula (V)

RSH (V)

wherein R has the same meaning as defined above,
in the presence of a base in a mixed medium of water and an aprotic polar solvent.

The substituted or unsubstituted aromatic group represented by Ar in the above formulae includes, for example, a group of the formula:

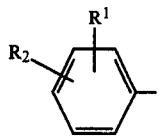

wherein $R^1$ and $R^2$ may be the same or different and each represent a hydrogen atom, an alkyl group, an aryl group, a halogen atom, a cyano group, a $OR^4$ group (in which $R^4$ represents a hydrogen atom, an alkyl group, an alkenyl group, an aryl group, an aralkyl group), a $SR^4$ group (in which $R^4$ is the same as defined above) or a

group (in which $R^5$ represents an alkyl group or an aryl group), or $R^1$ and $R^2$ may cooperate to form an alkylidenedioxy group such as a methylenedioxy group and a isopropylidenedioxy group, a group of the formula:

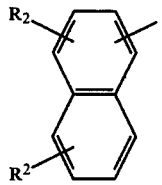

wherein $R^1$ and $R^2$ are the same as defined above, and a group of the formula:

wherein A represents an oxygen atom (O), a sulfur atom (S) or a >$NR^6$ group (in which $R^6$ is a hydrogen atom or a lower alkyl group having 1 to 4 carbon atoms), and $R^3$ represents a hydrogen atom, an alkyl group, an aryl group, a halogen atom, a cyano group, a

group (in which $R^5$ is the same as defined above).

A halogen atom represented by X in the above formulae includes a chlorine atom and a bromine atom. The three halogen atoms in formula (IV) may be the same or different.

The alkyl group represented by R in the above formulae may preferably be a lower alkyl group having 1 to 4 carbon atoms, such as methyl, ethyl, propyl, isopropyl, butyl, etc.

Accordingly, as the aromatic aldehyde used as a starting material in the process of this invention, there may be mentioned, for example, unsubstituted aromatic aldehyde such as benzaldehyde, thiophenealdehyde, furylaldehyde, pyrrolealdehyde, naphthylaldehyde and the like; (alkyl-substituted phenyl) aldehydes such as, tolualdehyde, ethylbenzaldehyde and the like; (aryl-substituted phenyl)aldehydes such as phenylbenzaldehyde; (mono- or dialkoxy-substituted phenyl)aldehydes and (aryloxy-substituted phenyl)aldehydes such as anisaldehyde, ethoxybenzaldehyde, allyloxybenzaldehyde, benzyloxybenzaldehyde, piperonal, phenyloxybenzaldehyde, and the like; (halo-substituted phenyl)aldehydes such as chlorobenzaldehyde, bromobenzaldehyde and the like; (alkyl, alkoxy, alkenyloxy or aryloxyhalo-di-substituted phenyl)-aldehydes such as, methylchlorobenzaldehyde, methoxychlorobenzaldehyde, allyloxychlorobenzaldehyde, phenoxychlorobenzaldehyde and the like; substituted naphtylaldehyde such as 6-methoxy-2-naphthylaldehyde, 5-halo-1-naphthylaldehyde, 2-methyl-1-naphthylaldehyde and the like; substituted thiophenealdehyde such as 5-chloro-2-thiophenealdehyde, 5-methyl-2-thiophenealdehyde, 5-benzoyl-2-thiophenealdehyde and the like; substituted furylaldehydes such as 5-methyl-2-furylaldehyde, 5-benzoyl-2-furylaldehyde and the like; substituted pyrrolealdehydes such as 1-methyl-5-toluoyl-2-pyrrolealdehyde, 1,5-dimethyl-2-pyrrolealdehyde, 1-methyl-5-toluoyl-3-pyrrolealdehyde. These aldehydes are easily available in industry.

Examples of trihalomethanes of formula (IV) above which can be used are tribromomethane, trichloromethane, dibromochloromethane, dichlorobromomethane and the like.

Examples of alkanethiols represented by formula (V) above used as starting material in the present invention are methanethiol, ethanethiol, propanethiol, butanethiol and the like. For ease in handling and availability, lower alkanethiols are preferably used.

Examples of alcohol derivatives represented by formula (III) used as starting materials of this invention are 1-phenyl-2,2,2-trichloroethanol, 1-methylphenyl-2,2,2-trichloroethanol, 1-ethylphenyl-2,2,2-trichloroethanol, 1-phenylphenyl-2,2,2-trichloroethanol, 1-methoxyphenyl-2,2,2-trichloroethanol, 1-ethoxyphenyl-2,2,2-trichloroethanol, 1-allyloxyphenyl-2,2,2-trichloroethanol, 1-benzyloxyphenyl-2,2,2-trichloroethanol, 1-methylenedioxyphenyl-2,2,2-trichloroethanol, 1-phenoxyphenyl-2,2,2-trichloroethanol, 1-chlorophenyl-2,2,2-trichloroethanol, 1-bromophenyl-2,2,2-trichloroethanol, 1-methylchlorophenyl-2,2,2-trichloroethanol, 1-ethylchlorophenyl-2,2,2-trichloroethanol, 1-methoxyphenyl-2,2,2-trichloroethanol, 1-allyloxychlorophenyl-2,2,2-trichloroethanol, 1-thienyl-2,2,2-trichloroethanol, 1-furyl-2,2,2-trichloroethanol, 1-naphthyl-2,2,2-trichloroethanol, 1-(1-methyl-5-toluoylpyryl-2)-2,2,2-trichloroethanol, 1-(1-methyl-5-toluoylpyryl-3)-2,2,2-trichloroethanol. These alcohol derivatives can easily be prepared by addition reaction of an aromatic hydrocarbon with a trihaloacetaldehyde [for example, F. D. Chattaway et al., J. Chem. Soc., 701 (1934); R. C. Blinn et al., J. Amer. Chem. Soc., 76, 37 (1954), etc.], or addition reaction of an aromatic aldehyde with haloform in the presence of a base [for example, E. D. Bergmann et al., J. Amer. Chem. Soc., 72, 5012 (1950), etc.].

It is essential to carry out the present invention in the presence of a base. Examples of bases are alkali metal hydroxides such as potassium hydroxide, sodium hydroxide, lithium hydroxide and the like and alkali metal carbonates such as sodium carbonate, potassium carbonate and the like. The use of alkali metal hydroxides is preferred from the standpoint that the reaction time can be shortened and the yield of the product can be improved.

Further it is essential to carry out this invention in a mixed medium of water and an aprotic polar solvent. Examples of aprotic polar solvents which can be used in a mixture with water are sulfoxides such as dimethyl sulfoxide and the like, sulfones such as sulforane and the like, amides such as dimethylformamide, dimethylacetamide, hexamethylphosphoramide and the like, nitriles such as acetonitrile and the like, ethers such as tetrahydrofuran, dimethoxyethane, diglyme and the like, or a mixture thereof. The use of dimethyl sulfoxide or acetonitrile is preferred in order to obtain the desired compound in high selectivity and high yield. From the standpoints of yield and reaction selectivity, water and an aprotic polar solvent are used at a ratio of 1:0.2–5 by volume, preferably 1:0.8–1.2, most preferably, 1:1 by volume.

The reaction is carried out by dissolving the compounds of formulae (II), (IV) and (V) or the compounds of formulae (III) and (V) in the above medium and then adding thereto a base dissolved in the above mixed medium, but the order of addition can be changed depending upon the type of the starting aldehyde (II) or the starting alcohol (III). The alkanethiol (V) is preferably used in an amount of not less than 2 times, preferably 2 to 7 times in molar equivalent with respect to the aromatic aldehyde (II) or alcohol derivative (III). The trihalomethane of formula (IV) is used in an equimolar amount to a slightly excess amount with respect to the aromatic aldehyde (II). The base is used in an amount of not less than 4 molar equivalents, preferably 4 to 8 molar equivalents, with respect to the starting material (II) or (III). The reaction does not require specific heating or cooling and proceeds easily at room temperature, but, if necessary, the reaction can be carried out with slightly cooling or heating to promote the reaction and to improve the yield.

According to the present invention, the aromatic acetic acid represented by formula (I) can be prepared from the aromatic aldehyde or alcohol represented by formula (II) or (III) respectively. Examples of aromatic acetic acids obtained by the present invention are (alkyl-substituted phenyl)acetic acids such as (methyl-substituted phenyl)acetic acid, (ethyl-substituted phenyl)acetic acid and the like, (aryl-substituted phenyl)acetic acids such as (phenyl-substituted phenyl)acetic acid and the like, (mono- or dialkoxy-substituted phenyl)acetic acids and (aryloxy-substituted phenyl)acetic acids such as (methoxy-substituted phenyl)acetic acid, (ethoxy-substituted phenyl)acetic acid, (allyloxy-substituted phenyl)acetic acid, (benzyloxy-substituted phenyl)acetic acid, (methylenedioxy-substituted phenyl)acetic acid, (phenoxy-substituted phenyl)acetic acid and the like, (halo-substituted phenyl)acetic acids such as (chloro-substituted phenyl)acetic acid, (bromo-substituted phenyl)acetic acid and the like, (alkyl- or alkoxy-, alkenyloxy-, aryloxyhalo-di-substituted phenyl)acetic acids such as (methoxychloro-di-substituted phenyl)acetic acid, (ethylchloro-di-substituted phenyl)acetic acid, (allyloxychloro-di-substituted phenyl)acetic acid, (phenoxy-chloro-di-substituted phenyl)acetic acid and the like, (aryl-substituted phenyl)acetic acid such as m-benzoyl-phenyl acetic acid, p-thenoyl-phenyl-acetic acid and the like, (alkyl or arylthio-substituted phenyl)acetic acid such as p-methylthiophenylacetic acid, p-phenylthio-phenylacetic acid and the like, substituted naphthylacetic acid such as 6-methoxy-2-naphthylacetic acid, 5-halo-1-naphthylacetic acid, 2-methyl-1-naphthylacetic acid and the like, substituted thiophenylacetic acid such as 5-chloro-2-thiophene-acetic acid, 5-methyl-2-thiophene-acetic acid, 5-benzoyl-2-thiophene-acetic acid and the like, substituted furylacetic acid such as 5-methyl-2-furylacetic acid, 5-benzoyl-2-furylacetic acid and the like, substituted pyrroleacetic acid such as 1-methyl-5-toluoyl-2-pyrroleacetic acid, 1,5-dimethyl-2-pyrroleacetic acid, 1-methyl-5-toluoyl-3-pyrroleacetic acid.

In considering the present invention from the reaction mechanism, the main reaction route for obtaining the aromatic acetic acids (I) from the aromatic aldehydes (II) or from the aromatic alcohol derivatives (III) can be represented by the following reaction scheme.

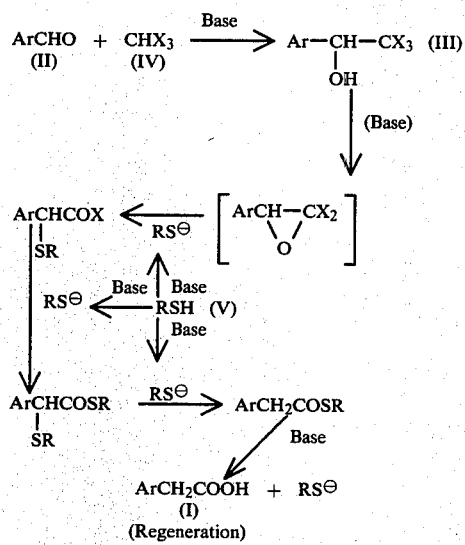

That is, the reaction in which are used an aromatic aldehyde and a trihalomethane as starting materials proceeds via the formation of a 2,2,2-trihalo-1-arylethanol by addition reaction of a trihalomethane to an aromatic aldehyde in the presence of a base, the formation of a dihalo epoxide by a base, the ring-opening reaction of the epoxide by a mercaptide anion, the cleavage of an α-thio substituent from a an α-thio-substituted aromatic acetic acid derivative by the mercaptide anion, hydrolysis, etc. The use of a highly nucleophilic alkanethiol (V) and the abovedescribed mixed medium which enables a smooth nucleophilic substitution reaction makes it easy that the mercaptide anion acts nucleophilically on the α-thio-substituted aromatic acetic acid derivative produced as intermediate, whereby the aromatic acetic acid in which the α-thio substituent has been removed can be obtained directly.

In the process of this invention starting from ArCHO, the reaction m ay preferably be performed without isolation of the intermediate compound, i.e., the alcohol derivative (III). However, it may be carried out after isolation of the alcohol derivative (III).

The present invention is further illustrated in greater detail by the following Examples and Comparative Examples.

EXAMPLE 1

To a 50% dimethyl sulfoxide aqueous solution (25 ml) were added, methyl mercaptan (0.95 g, 20 mmoles), an aqueous solution (5 ml) of potassium hydroxide (0.3 g, 5.3 mmoles), a dimethyl sulfoxide solution (5 ml) of o-benzyloxybenzaldehyde (1.06 g, 5 mmoles) and then bromoform (1.52 g, 6 mmoles) under ice-water cooling with stirring, and the mixture was stirred for 30 minutes. Potassium hydroxide (2.0 g, 35 mmoles) dissolved in a 50% dimethyl sulfoxide aqueous solution (15 ml) was added dropwise to the reaction mixture. After completion of the addition, the mixture was stirred at room temperature overnight and at 70° C. for 2 hours. After cooling to room temperature, water and diethyl ether were added thereto and the ether-soluble material was removed. The aqueous layer was rendered acidic with dilute hydrochloric acid and extracted with ethyl acetate. The extract was washed with water, dried over anhydrous magnesium sulfate and filtered. The filtrate was concentrated and purified by silica gel column chromatography to afford 0.78 g. of o-benzyloxyphenylacetic acid. Yield 64%.

NMR (CDCl$_3$, TMS): δ 3.68 (s, 2H), 5.03 (s, 2H), 6.73–7.53. (m, 9H), 10.7 (bs, 1H).

EXAMPLE 2

To a 50% dimethyl sulfoxide aqueous solution (50 ml) were added ethyl mercaptan (3.5 ml, 47 mmoles), an aqueous solution (10 ml) of potassium hydroxide (0.6 g, 10 mmoles), a solution of 2-thienyl aldehyde (1.12 g, 10 mmoles) in dimethyl sulfoxide (10 ml) and then bromoform (3.04 g, 12.2 mmoles) in an argon atmosphere under ice-water cooling with stirring, and the mixture was stirred for 1 hour. Potassium hydroxide (3.04 g, 46 mmoles) dissolved in a 50% dimethyl sulfoxide aqueous solution (30 ml) was added dropwise to the reaction mixture. After completion of the addition, the mixture was stirred for 2 hours and then at room temperature for 3 hours. Water and diethyl ether were added to the reaction mixture and the ether-soluble material was removed. The aqueous layer was rendered acidic with dilute hydrochloric acid and extracted with chloroform. The extract was washed with water, dried over anhydrous magnesium sulfate and filtered. The filtrate was concentrated and purified by silica gel chromatography to afford 0.82 g of thienylacetic acid. Yield 58%. m.p.: 60°–62° C. (Lit. 62°–64° C.)

NMR (CDCl$_3$, TMS): δ3.8 (s, 2H), 6.80–7.23 (m, 3H), 11.2 (bs, 1H).

EXAMPLE 3

To a 50% dimethyl sulfoxide aqueous solution (50 ml) were added methyl mercaptan (2.5 g, 52 mmoles), an aqueous solution (10 ml) of potassium hydroxide (0.6 g, 10 mmoles) a solution of p-methoxybenzaldehyde (1.36 g, 10 mmoles) in dimethyl sulfoxide (10 ml) and then bromoform (3.04 g, 12.2 mmoles) under ice-water cooling with stirring, and the mixture was stirred for one hour. Potassium hydroxide (3.04 g, 46 mmoles) dissolved in a 50% aqueous solution of dimethyl sulfoxide (30 ml) was added dropwise to the reaction mixture. After completion of the addition, the mixture was stirred overnight at room temperature and then 2 hours at 70° C. After allowing the mixture to cool to room temperature, water and diethyl ether were added to the reaction mixture and the ether-soluble material was removed. The aqueous layer was rendered acidic with dilute hydrochloric acid and extracted with ethyl acetate. The extract was washed with water, dried over anhydrous magnesium sulfate and filtered. The filtrate was concentrated and purified by silica gel chromatography to afford 1.64 g. of crystals. Upon measurement of NMR spectrum of the resulting crystals and gas-chromatographic determination of the corresponding methyl ester obtained by treating the crystals with diazomethane (2% EGA, 1 m, temperature increase at a rate of 1° C./min from 150° C.), the isolated crystals were found to be a mixture of p-methoxyphenylacetic acid and α-methylthio-p-methoxyphenylacetic acid at a ratio of 92:8. That is, the yield of p-methoxyphenylacetic acid was 87% based on p-methoxybenzaldehyde. The NMR spectrum of 4-methoxyphenylacetic acid in the crude product:

NMR (CDCl$_3$, TMS): δ 3.48 (s, 2H), 3.65 (s, 3H), 6.75 (d, J=9 Hz, 2H), 7.12 (d, J=9 Hz, 2H), 9.15 (s, 1H).

EXAMPLES 4–27

In the same manner as in Example 3, aromatic acetic acids were synthesized using the aromatic aldehydes as starting materials shown in the following reaction scheme. The results obtained are shown in Table I.

$$\text{Ar—CHO} \xrightarrow[\text{50\% Dimethyl Sulfoxide Aqueous Solution}]{\text{RSH (V), HCBr}_3\text{, Potassium Hydroxide}}$$
(II)

Ar—CH$_2$COOH
(I)

TABLE I

| Example | Ar | R | Yield (%) |
|---|---|---|---|
| 4 | Ph | Me | 52 |
| 5 | " | Et | 77 |
| 6 | " | n-Pr | 49 |
| 7 | " | i-Pr | 31 |
| 8 | " | t-Bu | 53 |
| 9 | CH$_3$—⟨○⟩— | Me | 57 |
| 10 | " | Et | 72 |
| 11 | " | n-Pr | 76 |
| 12 | " | i-Pr | 43 |
| 13 | " | t-Bu | 70 |
| 14 | Cl—⟨○⟩— | Me | 55 |
| 15 | " | Et | 82 |
| 16 | " | n-Pr | 71 |
| 17 | " | i-Pr | 73 |
| 18 | " | t-Bu | 35 |
| 19 | Cl—⟨○⟩—<br>|<br>MeO—⟨○⟩— | Et | 79 |
| 20 | " | n-Pr | 87 |
| 21 | " | i-Pr | 84 |
| 22 | " | t-Bu | 92 |

TABLE I-continued

| Example | Ar | R | Yield (%) |
|---------|----|----|-----------|
| 23 | 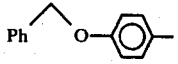 | Me | 30 |
| 24 | 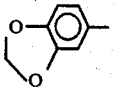 | Me | 58 |
| 25 |  | " | 64 |
| 26 | " | Et | 88 |
| 27 |  | Me | 59 |

Note:
The NMR spectra (CDCl$_3$, TMS) of the aromatic acetic acids in the crude products are as follows.

EXAMPLE 4

Phenylacetic acid: δ3.62 (s, 2H), 7.23 (bs, 5H), 10.4 (bs, 1H).

EXAMPLE 9 p-Methylphenylacetic acid; δ 2.30 (s, 3H), 3.55 (s, 2H), 7.10 (bs 4H), 11.2 (bs, 1H).

EXAMPLE 14 p-Chlorophenylacetic acid; δ 3.59 (s, 2H), 7.20 (bs, 4H), 11.32 (bs, 1H).

EXAMPLE 19 p-Methoxyphenylacetic acid; δ3.5 (s, 2H), 3.73 (s, 3H), 6.80 (d, J=9 Hz, 2H), 7.17 (d, J=9 Hz, 2H, 10.5 (bs, 1H).

EXAMPLE 23 p-Benzyloxyphenylacetic acid; δ 3.57 (s, 2H), 5.00 (s, 2H), 6.77-7.48 (m, 9H), 10.2 (bs, 1H).

EXAMPLE 24

3,4-Methylenedioxyphenylacetic acid; δ 3.52 (s, 2H), 5.90 (s, 2H), 6.50-7.03 (m, 3H), 9.83 (bs, 1H).

EXAMPLE 25

α-Naphthylacetic acid; 67 3.93 (s, 2H), 7.17-7.97 (m, 7H, 10.0 (bs, 1H).

EXAMPLE 27

α-Thienylacetic acid; δ3.75 (s, 2H), 6.75-7.25 (m, 3H), 10.3 (bs, 1H).

COMPARATIVE EXAMPLE 1

(Embodiment where i-propanol was used as a reaction solvent and the α-phenylthio group was not cleaved).

To a solution of thiophenol (1.65 g, 15 mmoles), bromoform (3.04 g, 12 mmoles), and p-methoxybenzaldehyde (1.4 g. 10 mmoles) dissolved in i-propanol (50 ml) was added a solution of potassium hydroxide (3.4 g, 53 mmoles) dissolved in i-propanol (50 ml) under ice-water cooling with stirring. After completion of the addition, the mixture was stirred overnight at room temperature and then refluxed for 3 hours. After allowing the mixture to cool to room temperatue, water and diethyl ether were added thereto to remove ether-soluble material. The aqueous layer was rendered acidic with dilute hydrochloric acid and extracted with chloroform. The extract was washed with water, dried over anhydrous magnesium sulfate and filtered. The filtrate was concentrated and purified by silica gel column chromatography to afford 2.69 g. of α-phenylthio-p-methoxyphenylacetic acid. Yield 96%.

NMR (CDCl$_3$, TMS): δ 3.74 (s, 3H), 4.79 (s, 1H), 7.02 (M, aromatic's H), 9.84 (bs, 1H).

COMPARATIVE EXAMPLE 2

(Embodiment where ethanol was used as a reaction solvent and the α-phenylthio group was not cleaved).

The experiment was conducted using the same starting materials and the same reaction procedures as used in Comparative Example 1 but using ethanol as a reaction solvent also results in the production of 2.35 g. of α-phenylthio-p-methoxyphenylacetic acid. Yield 85%.

EXAMPLE 28

To a mixed solvent of acetonitrile (25 ml) and water (10 ml) were aded 1-methyl-2-formyl-5-p-methylbenzylpyrrole (1.135 g, 5 mmoles), bromoform (1.54 g, 6.1 mmoles) and ethyl mercaptan (1.61 g, 26 mmoles, 1.94 ml). A solution of potassium hydroxide (1.57 g, 28 mmoles) dissolved in water (7.5 ml) and acetonitrile (25 ml) was added dropwise thereto at room temperature with stirring. After complete of the addition, the reaction mixture was stirred overnight at room temperature and heated with stirring at 80° C. in a hotwater bath for 2 hours. After allowing the mixture to cool to room temperature, water (50 ml) was added thereto, diluted and washed with ether. The aqueous layer was separated and acidified with HCl. The reaction mixture became white turbid to form a solid. This solid was extracted with ether, dried and concentrated to afford 0.9 g. of 5-p-methylbenzoyl-1-methylpyrrole-2-acetic acid. Yield 70%.

m.p.: 155°-156° C.

NMR (CDCl$_3$): δ 2.37 (s, 3H), 3.69 (s, 2H), 3.89 (s, 3H), 6.06 (d, J=4 Hz, 1H), 6.62 (d, J=4 Hz, 1H), 7.18 (d, 8 Hz, 2H), 7.66 (d, J=8 Hz, 2H).

IR (KBr): 3425, 2940, 2900, 1700, 1600 cm$^{-1}$.

EXAMPLE 29

A solution of methyl mercaptan (1.8 g, 37.5 mmoles) and 1-phenyl-2,2,2-trichloroethanol (1.13 g, 5 mmoles) in dimethyl sulfoxide (10ml) was added to a 50% aqueous solution of dimethyl sulfoxide (40 ml) under ice-water cooling with stirring. Then, potassium hydroxide (1.7 g, 26 mmoles) was dissolved in a 50% aqueous soluton of dimethyl sulfoxide (20 ml) and the solution was added dropwise to the above mixture. The mixture was stirred at room temperature for 2 hours and then heated at 70° C. for 2 hours. After allowing the mixture to cool to room temperature, water and diethyl ether were added to the mixture and the ether-soluble material was removed. The aqueous layer was rendered acidic with dilute hydrochloric acid and extracted with ethyl acetate. The extract was dried over anhydrous magnesium sulfate, concentrated under reduced pressure and purified by silica gel column chromatography to afford 0.61 g. of phenylacetic acid. Yield 90%.

m.p.: 75°-76° C. (Lit. 76.5° C.)

NMR (CDCl$_3$, TMS): δ 3.62 (s, 2H), 7.23 (s, 5H), 10.4 (bs, 1H).

EXAMPLE 30

A solution of methyl mercaptan (1.8 g, 37.5 mmoles) and 1-(4-methylphenyl)-2,2,2-trichloroethanol (1.19 g, 5 mmoles) in dimethyl sulfoxide (10 ml) was added to a 50% dimethyl sulfoxide aqueous solution (40 ml) under ice-water cooling with stirring. Then, potassium hydroxide (1.70 g, 26 mmoles) dissolved in a 50% dimethyl sulfoxide aqueous solution (20 ml) was added dropwise to the reaction mixture which was then stirred at room temperature for 2 hours and further at 70° C. for 2 hours. After allowing the mixture to cool to room temperature, water and diethyl ether were added to the mixture and the ether-soluble material was removed. The aqueous layer was rendered acidic with dilute hydrochloric acid and extracted with ethyl acetate. The extract was dried over anhydrous magnesium sulfate, concentrated under reduced pressure and purified by silica gel chromatography to afford 0.627 g. of crystals. The NMR measurement of the resulting crystals and the gas-chromatographic determination of the corresponding methyl ester obtained by treatment of the crystals with diazomethane (2% EGA, 1 m, temperature increase from 130° C. at a rate of 1° C./min) indicated that the isolated crystals were a mixture of p-methylphenylacetic acid and α-methylthio-p-methylphenylacetic acid at a ratio of 89:11. Thus, the yield of p-methylphenylacetic acid was 72% based on 1-(4-methylphenyl)-2,2,2-trichloroethanol.

The NMR spectrum of 4-methylphenylacetic acid in the crude product:

NMR (CDCl$_3$, TMS); δ 2.30 (s, 3H), 3.55 (s, 2H), 7.10 (bs, 4H), 11.20 (bs, 1H).

EXAMPLES 31-35

In the same manner as in Example 30, the preparation of aromatic acetic acids was conducted by the following reaction scheme, starting with a 2,2,2-trichloro-1-arylethanol. The results obtained are shown in Table II.

$$Ar-\underset{OH}{\underset{|}{CH}}-CCl_3 \xrightarrow[\text{50\% Dimethyl Sulfoxide Aqueous Solution}]{\text{RSH (V), Potassium Hydroxide}}$$

(III)

$$Ar-CH_2COOH$$

(I)

TABLE II

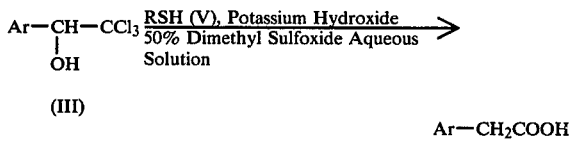

Ar = R$_1$—⟨phenyl with R$^2$⟩

| Example | R$_1$ | R$_2$ | R | Yield (%) |
|---|---|---|---|---|
| 31 | Cl— | H | Methyl | 96 |
| 32 | PhCH$_2$O— | H | Methyl | 57 |
| 33 | MeO— | H | Ethyl | 66 |
| 34 | O-allyl | Cl | Ethyl | 77 |
| 35 | Ar = thienyl | | Ethyl | 83 |

Note:
The NMR spectra (CDCl$_3$, TMS) and the melting points of the aromatic acetic acids in the crude products are as follows.

EXAMPLE 31 p-Chlorophenylacetic acid; δ 3.56 (s, 2H), 7.20 (bs, 4H), 11.10 (bs, 1H).

m.p.: 100°-102° C.

EXAMPLE 32 p-Benzyloxyphenylacetic acid; δ 3.52 (s, 2H), 4.92 (s, 2H), 6.72-7.70 (m, 9H), 8.52 (bs, 1H).

EXAMPLE 33 p-Methoxyphenylacetic acid; δ 3.48 (s, 2H), 3.67 (s, 3H), 6.80 (d, J=9Hz, 2H), 7.17 (d, J=9Hz, 2H), 10.9 (bs, 1H).

EXAMPLE 34

3-Chloro-4-allyloxyphenylacetic acid (Alchlofenac); δ 3.53 (s, 2H), 4.55 (bd, J=5Hz, 2H), 5.03-5.60 (m, 2H), 6.40-5.67 (m, 1H), 6.73-7.50 (m, 4H).

m.p.: 91°-93° C. (Lit. 92°-94° C.)

EXAMPLE 35

α-Thienylacetic acid; δ 3.80 (s, 2H), 6.80-7.23 (m, 3H), 11.2 (bs, 1H).

m.p.: 61°-63° C. (Lit. 62°-64° C.)

EXAMPLE 36

1-Methyl-2-(2,2,2-trichloro-1-hydroxyethyl)-5-p-toluoylpyrrole (150 mg, 0.43 mmole) was dissolved in dimethyl sulfoxide (3 ml) and water (3 ml), and ethyl mercaptan (187 mg, 3 mmoles) were added to the solution. To the mixture was added potassium hydroxide (142 mg, 2.2 mmoles) dissolved in a 50% dimethyl sulfoxide aqueous solution (2 ml) under ice-water cooling with stirring. The temperature of the mixture was slowly increased to room temperature followed by stirring overnight. The mixture was further stirred for 2 hours at 70° C. and allowed to cool to room temperature. Water (50 ml) and ethyl acetate (50 ml) were added thereto and the organic layer was separated. The aqueous layer was rendered acidic with dilute hydrochloric acid to afford white crystals which were extracted with ethyl acetate (100 ml). The extract was washed with water, dried over anhydrous magnesium sulfate and filtered. The filtrate was concentrated to afford 77 mg. of 1-methyl-5-p-toluoylpyrrole-2-acetic acid (tolmetin) as light yellow crystals. Yield 70%.

NMR (CDCl$_3$); δ 2.37 (s, 3H), 3.69 (s, 2H), 3.89 (s, 3H), 6.06 (d, J=4Hz, 1H), 6.62 (d, J=4Hz, 1H), 7.18 (d, J=8Hz, 2H), 7.66 (d, J=8Hz, 2H).

IR (KBr); 3425 2940, 2900, 1700, 1600 cm$^{-1}$.

EXAMPLE 37

1-Methyl-2-(2,2,2-trichloro-1-hydroxyethyl)-5-p-toluoylpyrrole (347 mg, 1 mmol) was dissolved in dimethyl sulfoxide (4 ml) and then to this were added water (4 ml) and methyl mercaptan (241 mg, 5 mmoles). Potassium hydroxide (329 mg, 5 mmoles) dissolved in a 50% dimethyl sulfoxide aqueous solution (2 ml) was added to the mixture. The mixture was gradually heated to room temperature and then stirred overnight and furthermore at 70° C. for 4 hours. After allowing the mixture to cool to room temperature, water (50 ml) and ethyl acetate (50 ml) were added to the mixture to separate the organic layer. The aqueous layer was acidified with dilute HCl, extracted with ethyl acetate (100 ml), washed with water and dried over anhydrous magnesium sulfate. After filtration, the filtrate was concentrated to afford 229 mg. of 1-methyl-5-p-toluoylpyrrole-2-acetic acid (tolmetin) as pale yellow crystals. Yield 89%.

EXAMPLE 38

1-Methyl-3-(2,2,2-trichloro-1-hydroxyethyl)-5-p-toluoylpyrrole (1.52 g, 44 mmoles) was dissolved in dimethyl sulfoxide (30 ml), and ethyl mercaptan (2.16 ml) and water (30 ml) were added thereto. To the resulting reaction mixture was added dropwise a 50% dimethyl sulfoxide solution (20 ml) of potassium hydroxide (1.26 g, 22.5 mmoles) under cooling in an ice-water bath. After completion of the addition, the ice-water bath was removed and the mixture was stirred at room temperature for 12 hours and at 80° C. for 3 hours. The reaction mixture was cooled to room temperature, diluted with water (50 ml) and washed with ethyl acetate. The aqueous layer was separated, rendered acidic with concentrated hydrochloric acid and the liberated acid was extracted with ethyl acetate. The extract was washed with water, dried over anhydrous magnesium sulfate, concentrated and purified by column chromatography (silica gel, ethyl acetate:n-hexane=1:1 v/v) to afford 0.87 g. of 1-methyl-5-p-toluoylpyrrole-3-acetic acid as light yellow crystals. Yield 77%.

m.p.: 139°–140° C.

NMR (CDCl$_3$); δ 2.36 (s, 3H), 3.44 (s, 2H), 3.86 (s, 3H), 6.62 (d, J=2Hz, 1H), 6.83 (d, J=2Hz, 1H) 7.17 (d, J=8Hz, 2H), 7.65 (d, J=8Hz, 2H).

IR (KBr disk); 1730, 1605, 1415, 1280, 1210, 1165, 925, 755 cm$^{-1}$.

COMPARATIVE EXAMPLE 3

(Embodiment where ethanol was used as a reaction solvent and the α-methylthio group was not cleaved).

A 20% aqueous solution of methyl mercaptan sodium salt (12.0 g, 34 mmoles) and potassium hydroxide (4.2 g, 66 mmoles) were dissolved in ethanol (25 ml). To the resulting mixture was added dropwise 1-(4-chlorophenyl)-2,2,2-trichloroethanol (4.0 g, 15.5 mmoles) dissolved in ethanol (10 ml) under water-cooling, and the mixture was stirred at room temperature for one day. Water and diethyl ether were added to remove any ether-soluble materials. The aqueous layer was rendered acidic with dilute hydrochloric acid, extracted with ethyl acetate, washed with water and dried over anhydrous magnesium sulfate. After filtration, the filtrate was concentrated and purified by silica gel column chromatography to afford 2.1 g of α-methylthio-p-chlorophenylacetic acid. Yield 62%.

NMR (CDCl$_3$, TMS); δ 2.10 (s, 3H), 4.42 (s, 1H), 7.32 (s, 4H), 11.33 (bs, 1H).

COMPARATIVE EXAMPLE 4

(Embodiment where methanol was used as a reaction solvent and the α-phenylthio group was not cleaved).

Potassium hydroxide (1.12 g, 20 mmoles) was dissolved in methanol (10 ml) in an argon atmosphere and thiophenol (0.6 g, 5.54 mmoles) was added thereto under ice cooling with stirring. After 10 minutes, α-trichloromethyl-2-thiophenemethanol (1.16 g, 5 mmoles) dissolved in methanol (3 ml) was added to the mixture. Ten minutes after completion of the addition, the temperature of the mixture was gradually increased and the mixture was heated under reflux for 2 hours with vigorous stirring. After allowing the mixture to cool to room temperature, most of the solvent was removed by distillation under reduced pressure, and diethyl ether was added to the residue. The mixture was decomposed with dilute hydrochloric acid, and the ether layer was separated, washed with water, dried over anhydrous magnesium sulfate and filtered. The filtrate was concentrated under reduced pressure and the resulting residue was purified by silica gel column chromatography (ethyl acetate:n-hexane=1:4) to afford 940 mg. of α-phenylthio-2-thiopheneacetic acid as a viscous oily substance. Yield 76%.

IR (Neat); 3060, 1715, 1587, 1485, 1440, 1416, 1253, 750, 705, 694 cm$^{-1}$.

NMR (CDCl$_3$, TMS); δ 5.03 (s, 1H), 6.62–7.60 (m, 8H), 11.47 (s, 1H).

COMPARATIVE EXAMPLE 5

(Embodiment where a water-methanol solvent system was used and the α-methylthio group was not cleaved).

A 20% aqueous solution of sodium methylthiolate (2.0 g, 5.7 mmoles) and potassium hydroxide (670 mg, 12 mmoles) were added to methanol (5 ml). To the resulting mixture was added 1-(3-chloro-4-allyloxyphenyl)-2,2,2-trichloroethanol (948 mg, 3 mmoles) dissolved in methanol (1.5 ml) in an argon atmosphere under ice-water cooling with stirring, and the reaction mixture was heated under reflux for 2.5 hours. After allowing the mixture to cool to room temperature, most of the solvent was removed by distillation under reduced pressure and diethyl ether was added to the residue. The mixture was decomposed with dilute hydrochloric acid, and the ether layer was separated, dried over anhydrous magnesium sulfate and filtered. The filtrate was concentrated to afford 670 mg. of α-methylthio-3-chloro-4-allyloxyphenylacetic acid as crystals. A sample for the elementary analysis was purified by recrystallization from ethyl acetate-n-hexane. Yield 82%.

m.p.: 94°–95° C.

IR (KBr); 1720, 1700, 1647, 1570, 1500, 1290, 1260, 1174, 1000, 987, 922, 914 cm$^{-1}$.

NMR (CDCl$_3$, TMS); δ 2.07 (s, 3H), 4.35 (S, 1H), 4.54 (bd, J=4Hz, 2H), 5.14–5.51 (m, 2H), 5.80–6.29 (m, 1H), 6.79–7.51 (m, 3H), 10.73 (bs, 1H).

MS m/e (%); 272 (15), 225 (26), 41 (100).

Anal. Calcd. for $C_{12}H_{13}ClO_3S$: C, 56.15; H, 5.11%: Found: C, 55.95; H, 5.25%.

We claim:

1. A process for preparing an aromatic acetic acid represented by the formula

wherein Ar is a substituted or unsubstituted aromatic selected from the group consisting of the following groups (a), (b) and (c):

(a) a group of the formula

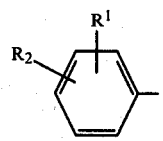

wherein $R^1$ and $R^2$ may be at the same or different and each represent a hydrogen atom, a lower alkyl group, a lower alkoxy group, a halogen atom, a phenoxy group, a benzyloxy group or $R^1$ and $R^2$ may cooperate to form a lower alkylidenedioxy group;

(b) a group of the formula:

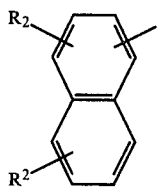

wherein $R^1$ and $R^2$ are the same as defined above; and (c) a group of the formula

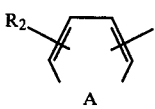

wherein A represents an oxygen atom (O), a sulfur atom (S) or a $>NR^6$ group in which $R^6$ is a hydrogen atom or a lower alkyl group having 1 to 4 carbon atoms, and $R^3$ represents a hydrogen atom or a lower alkyl substituted benzoyl group;

which comprises reacting an aromatic aldehyde represented by the formula

ArCHO wherein Ar has the same meaning as defined above, with a trihalomethane represented by the formula $HCX_3$ wherein X represents at least one halogen selected from the group consisting of chlorine and bromine atoms, in the presence of a base in a mixed medium of water and an aprotic polar solvent to form an alcohol derivative represented by the formula $$Ar-\underset{\underset{OH}{|}}{CH}-CX_3$$

wherein Ar has the same medium as defined above, and then reacting the thus formed alcohol derivative with an alkanethiol represented by the formula

RSH wherein R is an alkyl group,
in the presence of a base in a mixed medium of water and an aprotic polar solvent, wherein the volume ratio of said water and said aprotic polar solvent is 1:0.2–1:5.

2. A process according to claim 1 wherein said reaction is carried out without isolation of said alcohol derivative.

3. A process according to claim 1 or 2 wherein said base is used in an amount of 4 to 8 molar equivalents with respect to said aromatic aldehyde.

4. A process according to claim 1 or 2 wherein the volume ratio of said water and said aprotic polar solvent is 1:0.8–1:1.2.

5. A process according to claim 1 or 2 wherein said base is an alkali metal hydroxide.

6. A process according to claim 1 or 2 wherein R is a lower alkyl group having 1 to 4 carbon atoms.

7. A process according to claim 1 or 2 wherein said aprotic polar solvent is dimethyl sulfoxide or acetonitrile.

8. A process for preparting an aromatic acetic acid represented by the formula $ArCH_2COOH$ wherein Ar represents a substituted or unsubstituted aromatic group selected from the group consisting of the following groups (a), (b) and (c):

(a) a group of the formula:

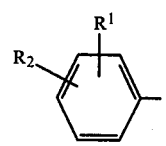

wherein $R^1$ and $R^2$ may be the same or different and each represent a hydrogen atom, a lower akyl group, a lower alkoxy group, a halogen atom, a phenoxy group, a benzyloxy group or $R^1$ and $R^2$ may cooperate to form a lower alkylidenedioxy group;

(b) a group of the formula:

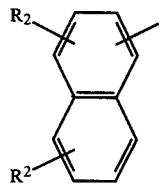

wherein $R^1$ and $R^2$ are the same as defined above; and (c) a group of the formula:

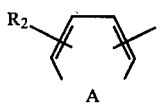

wherein A represents an oxygen atom (O), a sulfur atom (S) or a $>NR^6$ group in which $R^6$ is a hydrogen atom or a lower alkyl group having from 1 to 4 carbon atoms, and $R^3$ a represents a hydrogen atom or a lower alkyl substituted benzoyl group;

which comprises reacting an alcohol derivative represented by the formula $$Ar-\underset{\underset{OH}{|}}{CH}-CX_3$$

wherein Ar has the same meaning as defined above, and X represents a halogen atom, with an alkanethiol represented by the formula

RSH wherein R represents an alkyl group,
in the presence of a base in a mixed medium of water and an aprotic polar solvent, wherein the volume ratio of said water and said aprotic polar solvent is 1:0.2–1:5.

9. A process according to claim 8 wherein said base is used in an amount of 4 to 8 molar equivalents with respect to said alcohol derivative.

10. A process according to claim 8 or 9 wherein the volume ratio of said water and said aprotic polar solvent is 1:0.8–1:12.

11. A process according to claim 8 or 9 wherein said base is an alkali metal hydroxide.

12. A process according to claim 8 or 9 wherein R is a lower alkyl group having 1 to 4 carbon atoms.

13. A process according to claim 8 or 9 wherein said aprotic polar solvent is dimethyl sulfoxide or acetonitrile.

14. A process according to claim 10, wherein R is a lower alkyl group having 1 to 4 carbon atoms.

15. A process according to claim 14, wherein said base is an alkali metal hydroxide.

16. A process according to claim 15, wherein said aprotic polar solvent is dimethyl sulfoxide or acetonitrile.

17. A process according to claim 10, wherein said aprotic polar solvent is dimethyl sulfoxide or acetonitrile.

18. A process according to claim 4, wherein R is a lower alkyl group having 1 to 4 carbon atoms.

19. A process according to claim 18, wherein said base is an alkali metal hydroxide.

20. A process according to claim 19, wherein said aprotic polar solvent is dimethyl sulfoxide or acetonitrile.

21. A process according to claim 4, wherein said aprotic polar solvent is dimethyl sulfoxide or acetonitrile.

22. The process of claim 1 or 8, wherein said aromatic group is a chloro- or bromo-substituted group.

* * * * *

UNITED STATES PATENT AND TRADEMARK OFFICE
CERTIFICATE OF CORRECTION

PATENT NO. : 4,268,442
DATED : May 19, 1981
INVENTOR(S) : KONDO et al

It is certified that error appears in the above—identified patent and that said Letters Patent is hereby corrected as shown below:

Column 3, line 47, in the formula replace "$R_2$" with --$R^1$--.

Column 3, line 58, in the formula replace "$R_2$" with --$R^3$--.

Column 8, lines 65-70, delete the six symbols appearing to the right of the Example number column and to the left of the Ar formula column.

Column 10, line 19, delete "85%" and insert --84%--.

Column 10, line 54, rewrite "soluton" as --solution--.

Column 15, line 6, in the formula replace "$R_2$" with --$R^1$--.

Column 15, line 20, in the formula replace "$R_2$" with --$R^3$--.

Column 16, line 33, in the formula replace "$R_2$" with --$R^1$--.

Column 16, line 46, in the formula replace "$R_2$" with --$R^3$--.

Signed and Sealed this

Eighth Day of June 1982

[SEAL]

Attest:

Attesting Officer

GERALD J. MOSSINGHOFF

Commissioner of Patents and Trademarks